United States Patent [19]

Humphrey

[11] 4,015,899

[45] Apr. 5, 1977

[54] EYE TEST APPARATUS WITH PHYSICIAN ROUTED PATIENT INPUT ADJUSTMENT TO VARIABLE OPTICAL ELEMENTS

[75] Inventor: William E. Humphrey, Oakland, Calif.

[73] Assignee: Humphrey Instruments, Inc., Berkeley, Calif.

[22] Filed: Oct. 22, 1975

[21] Appl. No.: 624,808

[52] U.S. Cl. .................................. 351/17; 351/18; 351/26; 351/30

[51] Int. Cl.² ......................................... A61B 3/02

[58] Field of Search .................. 351/17, 18, 21, 30, 351/36, 26

[56] References Cited

UNITED STATES PATENTS

| | | | |
|---|---|---|---|
| 3,737,217 | 6/1973 | Haines et al. | 351/30 |
| 3,874,774 | 4/1975 | Humphrey | 351/30 |
| 3,905,688 | 9/1975 | Decker et al. | 351/30 |

*Primary Examiner*—Saxfield Chatmon, Jr.
*Attorney, Agent, or Firm*—Townsend and Townsend

[57] ABSTRACT

Corrective optics having continuously variable spherical, astigmatic, and prismatic functions are placed in a light path between a viewing patient and a projected target. Typically, the target is projected by a projector preferably through focusing optics in the form of a field mirror. The focusing optics serve the dual purpose of relaying to the patient the image of the target as well as focusing to the patient's eyeglass position a real image of the corrective optics. A patient has a patient input, typically a hand wheel, at or near his patient viewing station. The patient uses this input to vary the setting of the corrective optics. The eye examiner, at an adjacent eye examination station, is provided with a gear box having a clutch mechanism. The gear box includes examiner inputs for astigmatic and spherical correction to each eye as well as prismatic correction for both eyes. Through use of the clutch mechanism, the patient input at the patient viewing station can be routed individually or collectively to the various spherical, astigmatic, and prismatic corrections for either or both eyes. By utilizing specialized aligned targets and following simplified examiner instructions, direct patient input from the hand of the patient on the patient hand wheel into the variable spherical, astigmatic and prismatic optics is possible. Such input is specifically routed by the examiner to greatly decrease the time necessary for complete examination and eliminate much communication required for examination.

12 Claims, 9 Drawing Figures

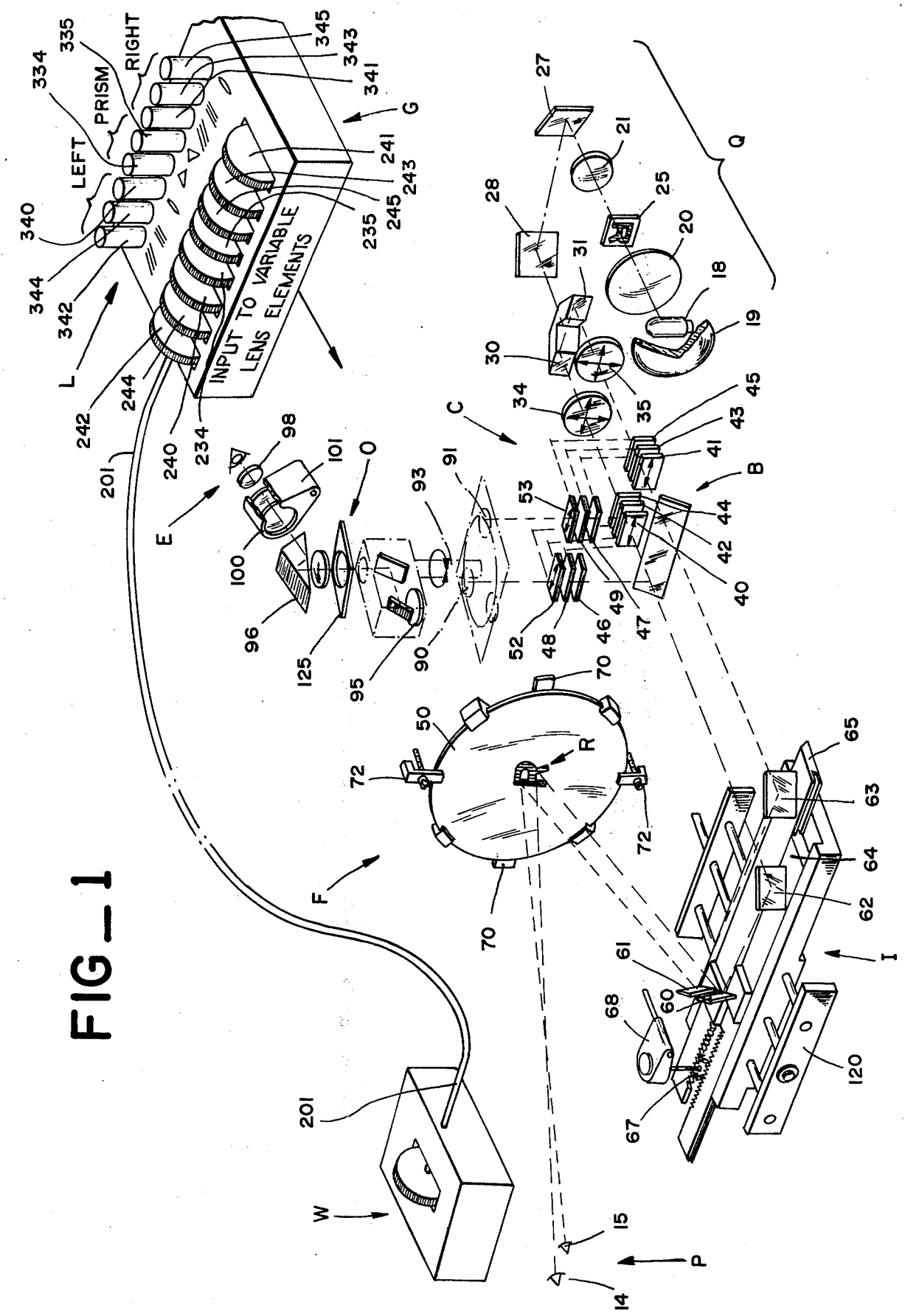

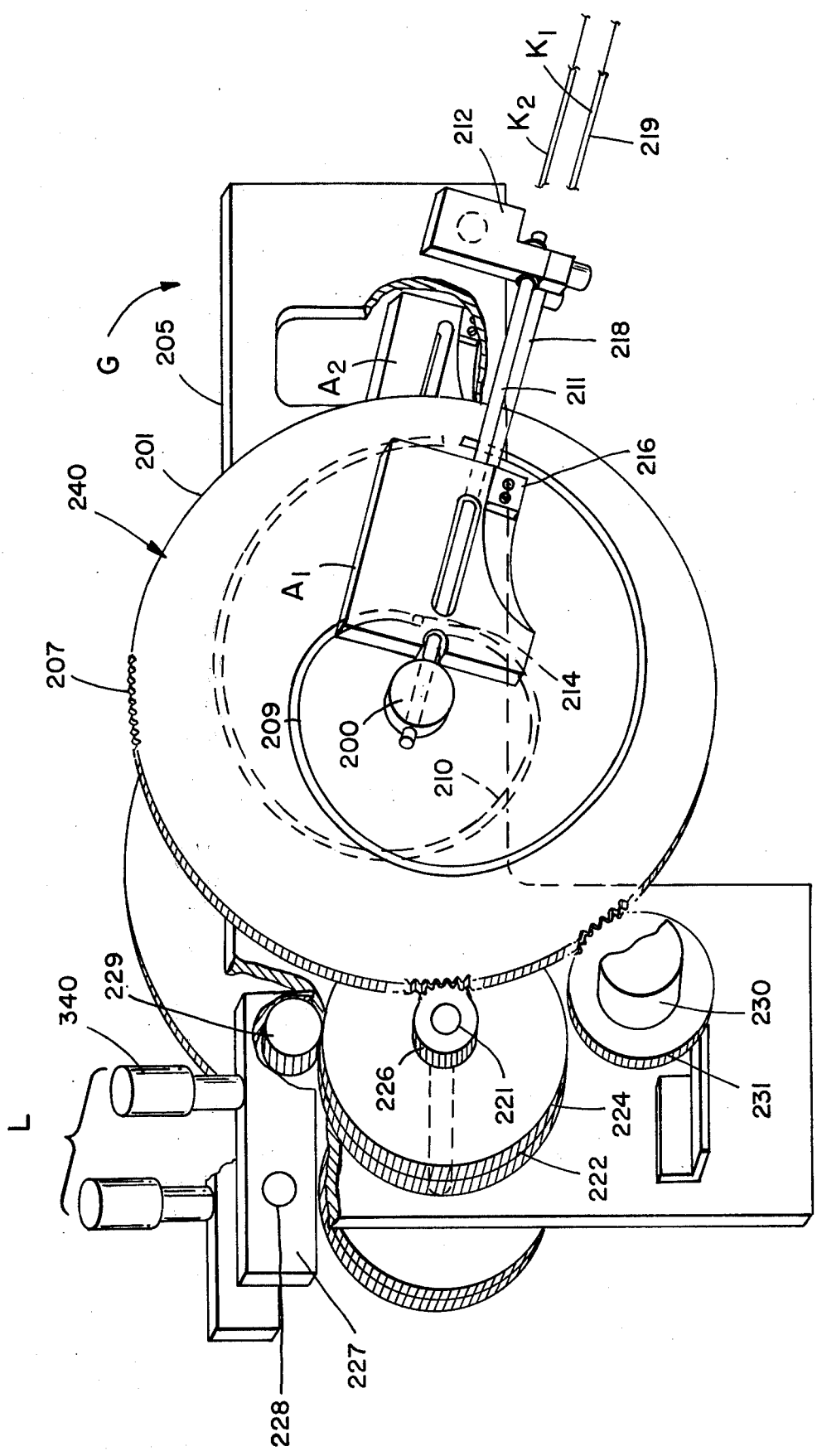
FIG_2

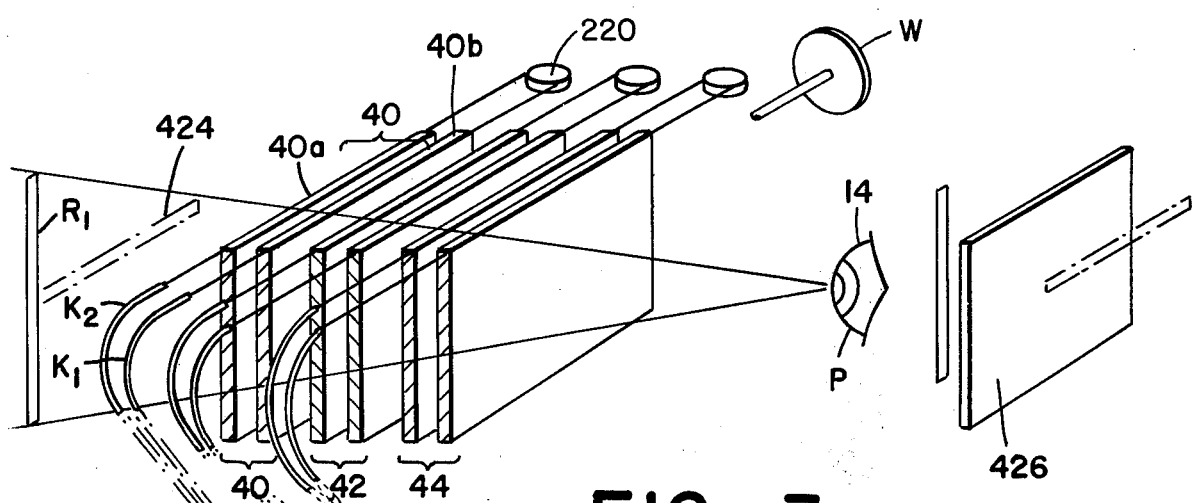
FIG_3
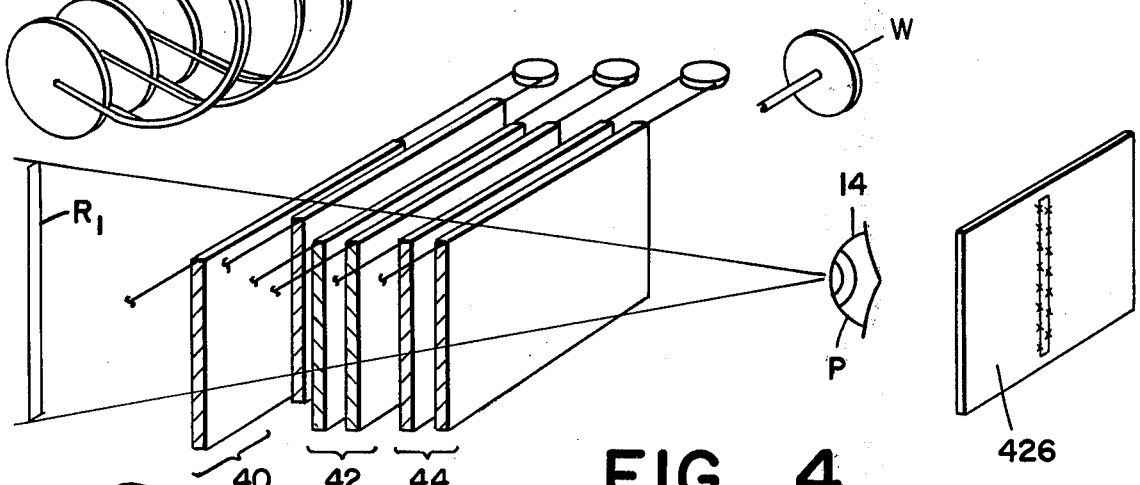
FIG_4
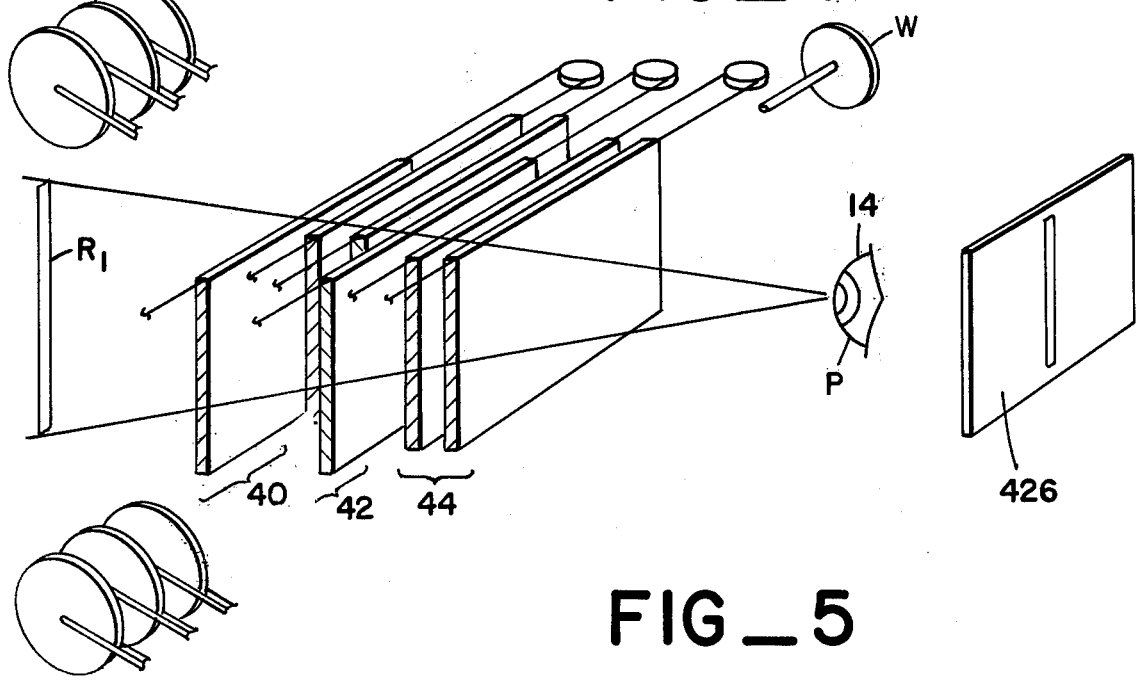
FIG_5

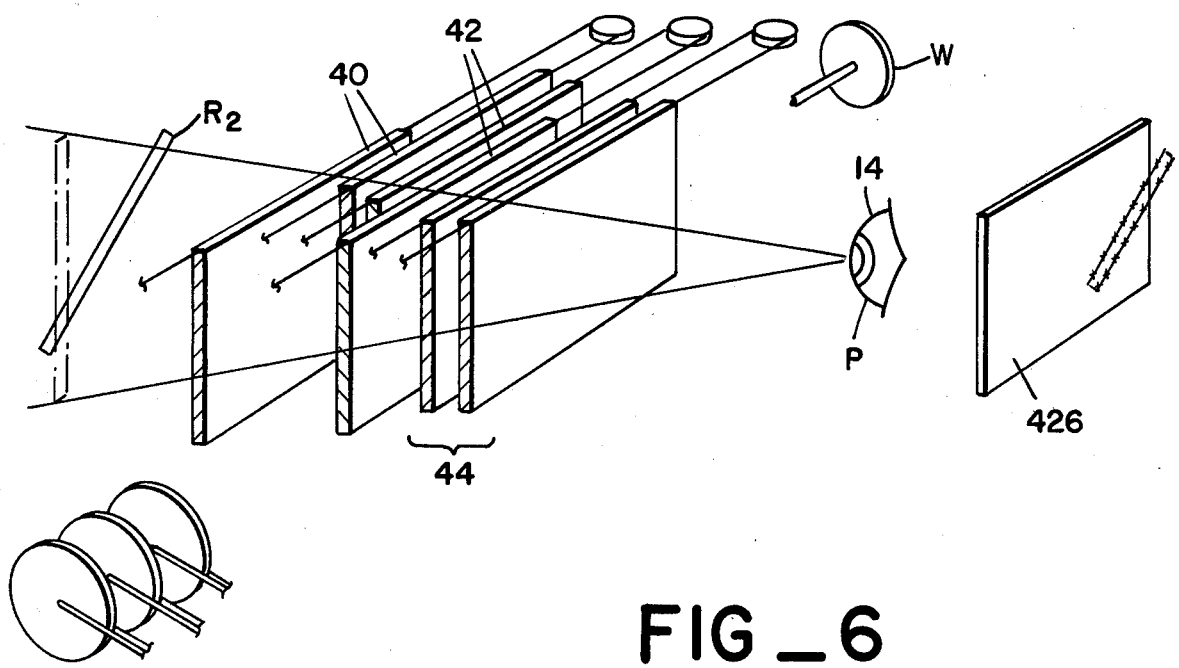
FIG_6
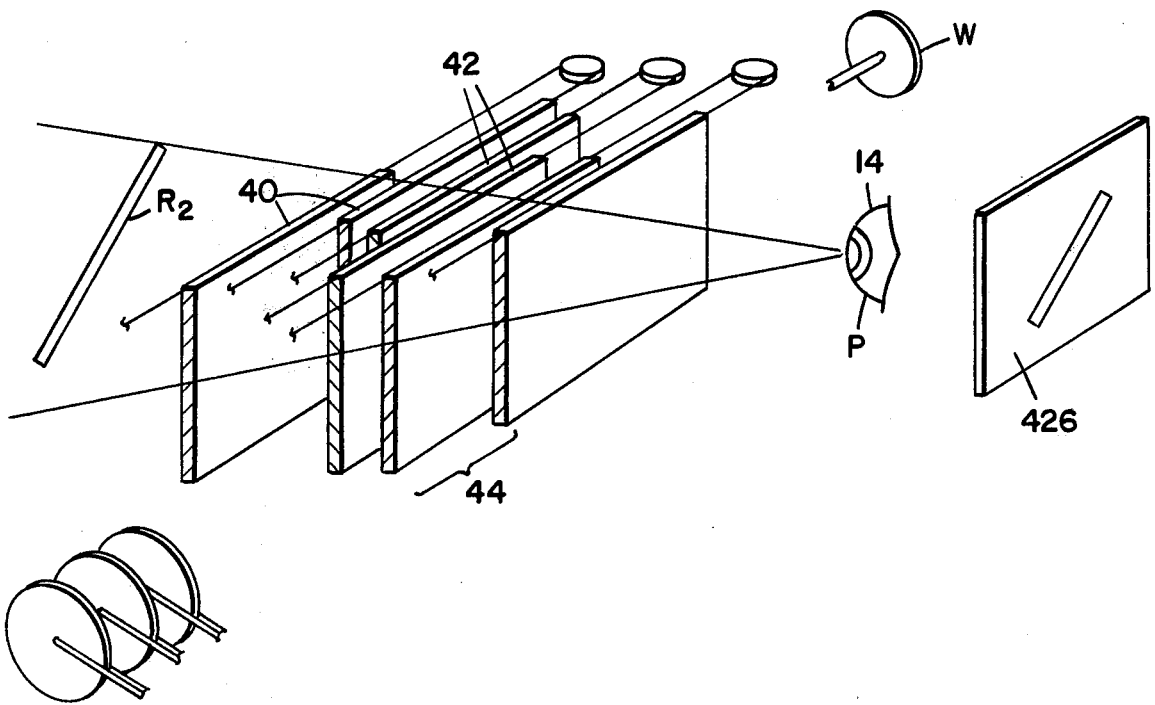
FIG_7

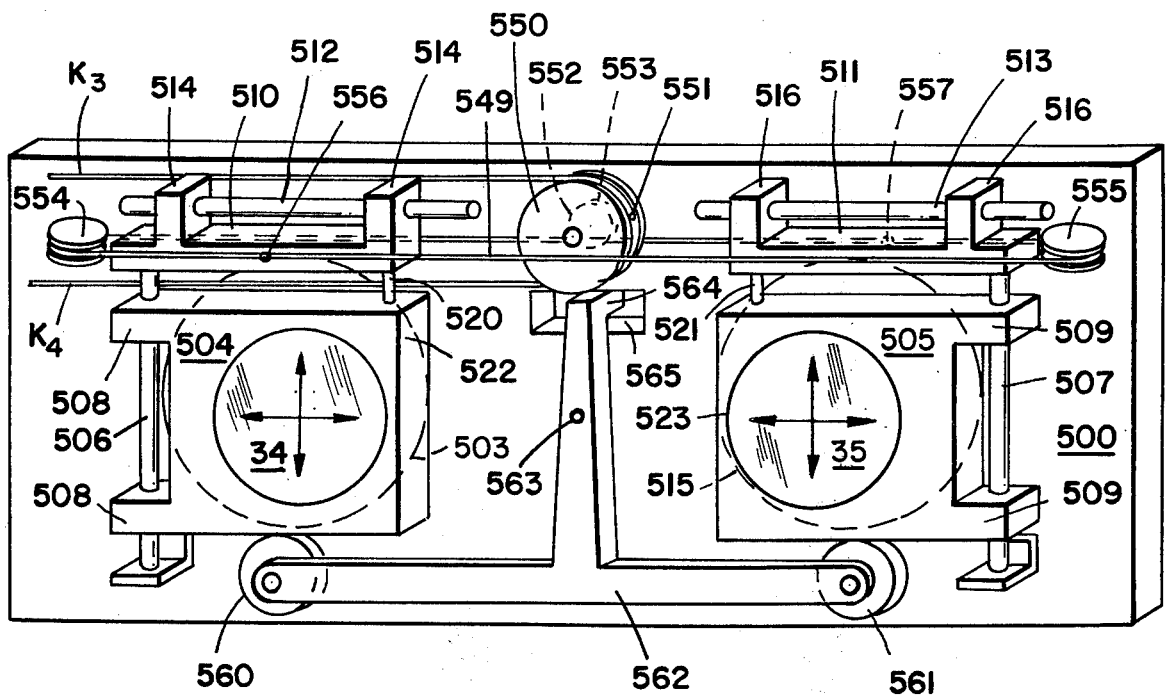
FIG_8
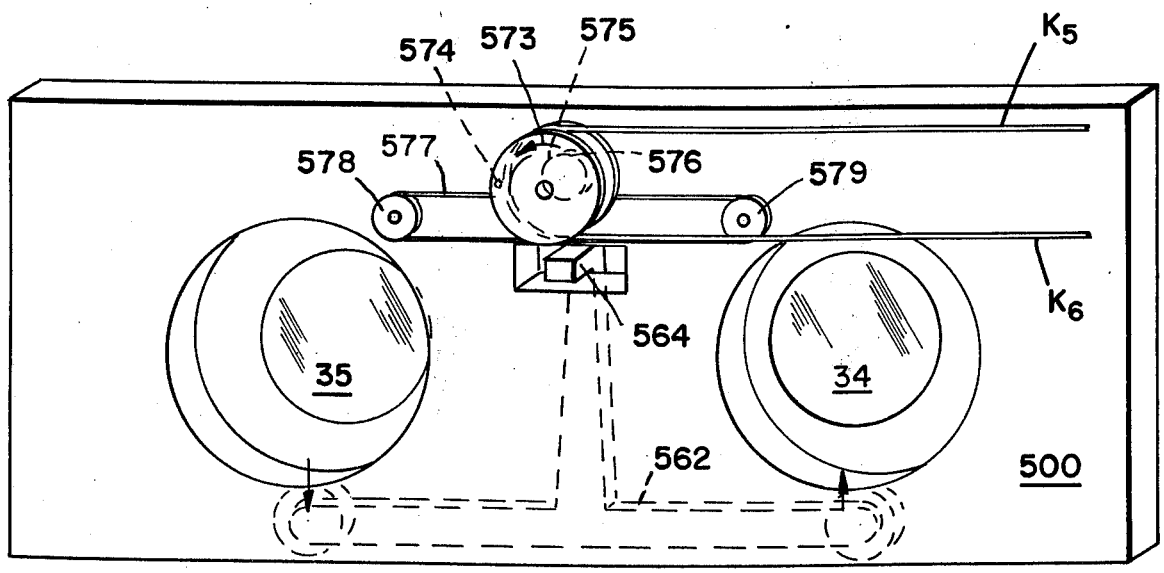
FIG_9

EYE TEST APPARATUS WITH PHYSICIAN ROUTED PATIENT INPUT ADJUSTMENT TO VARIABLE OPTICAL ELEMENTS

This invention relates to eye testing machinery and more specifically to an eye test apparatus with an examiner routed patient input to spherical, astigmatic, and prismatic optics.

SUMMARY OF THE PRIOR ART

Variable spherical and astigmatic lenses are known. See Luis W. Alvarez U.S. Pat. No. 3,305,294, issued Feb. 21, 1967, entitled "Two-Element Variable-Power Spherical Lens;" Luis W. Alvarez and William E. Humphrey U.S. Pat. No. 3,507,565, issued Apr. 21, 1970, entitled "Variable-Power Lens and System;" and, William E. Humphrey U.S. Pat. No. 3,751,138, issued Aug. 7, 1973, entitled "Variable Anamorphic Lens and Method for Constructing Lens."

Eye test apparatus is also known wherein the image of corrective optics is remotely broadcast to the eyeglass location of a patient through a field mirror or lens. See William E. Humphrey U.S. Pat. No. 3,874,774, issued Apr. 1, 1975, entitled "Eye Testing Apparatus."

Heretofore, manipulation and determination of the subjective optical correction during eye examination has almost always been the sole function of the eye examiner, whether he is an optometrist or ophthalmologist. The sequence of an examination usually comprises a general instruction followed by a change of the lens elements by the eye examiner. Prefatory to the questions, the eye examiner explains the particular function of the target or targets used during the examination. Thereafter, the examiner manipulates the corrective optics and the patient is asked whether his view is improved or not improved. This method may be conveniently referred to as the "see better - see worse" method. Typically, by bracketing patient responses with varying optical corrections and having the detected error sequentially reduced, optical correction is eventually determined on a more or less trial and error basis with the examiner manipulating and the patient responding.

The old see better - see worse system has at least two distinct disadvantages. First, time is not only consumed in explaining rather complex targets to the patient, but additionally in the physician-patient interchange of the see better - see worse information. The time lost between the communication, the eye examiner manipulation, and the succeeding communication lengthens the examination process.

Moreover, the manual dexterity of the patient is completely ignored even though the patient may be an experienced adult accustomed to adjustments of many optical devices such as binoculars and the like. These possible inputs of the patient have heretofore been ignored, especially with respect to the determination of astigmatism and prism.

SUMMARY OF THE INVENTION

Corrective optics having continuously variable spherical, astigmatic, and prismatic functions are placed in a light path between a viewing patient and a projected target. Typically, the target is projected by a projector preferably through focusing optics in the form of a field mirror. The focusing optics serve the dual purpose of relaying to the patient the image of the target as well as focusing to the patient's eyeglass position a real image of the corrective optics. A patient has a patient input, typically a hand wheel, at or near his patient viewing station. The patient uses this input to vary the setting of the corrective optics. The eye examiner, at an adjacent eye examination station, is provided with a gear box having a clutch mechanism. The gear box includes examiner inputs for astigmatic and spherical correction to teach eye as well as prismatic correction for both eyes. Through use of the clutch mechanism, the patient input at the patient viewing station can be routed individually or collectively to the various spherical, astigmatic, and prismatic corrections for either or both eyes. By utilizing specialized aligned targets and following simplified examiner instructions, direct patient input from the hand of the patient on the patient hand wheel into the variable spherical, astigmatic and prismatic optics is possible. Such input is specifically routed by the examiner to greatly decrease the time necessary for complete examination and eliminate such communication otherwise required.

OBJECTS AND ADVANTAGES OF THE INVENTION

An object of this invention is to provide for patient input into the process of optical examination. According to this aspect, the patient being examined is provided with a hand wheel. The hand wheel communicates through a clutch in the eye examiner gear box to optical elements for spherical, astigmatic and prismatic corrections in the patient target view path. By the expedient of having the eye examiner route the patient input at his gear box to specific spherical, astigmatic and prism inputs, direct patient input to optical corrections is provided.

An advantage of this aspect of the invention is that it eliminates one whole level of see better - see worse patient-eye examiner communication. A patient can be instructed to vary optical corrections himself.

A further advantage of direct patient input is that patient involvement in the prescription process can eliminate much anxiety. For example, instead of being subjected to an examination in a passive mode, the patient becomes physically as well as mentally cooperative with the examiner. The physical act of adding adjustment to his own refractive correction masks over anxieties which the patient might otherwise have, resulting in a better examination with less extraneous and nervous inputs.

A further advantage of this invention is that the manual dexterity of the patient can be used to determine his own prescription. As modern society includes many minute hand adjustments in day-to-day living, the acquired dexterity of the patient in making such adjustments can now be channeled to eyeglass prescription. Manual dexterity skills common in a large fraction of the population can be used to supplement eyeglass prescription by the eye examiner.

A further object of this invention is to disclose the use of special eye targets which, when used in combination with patient input, can readily result in a successful examination. Such targets have heretofore been disclosed in my U.S. Patent application Ser. No. 452,232, filed Mar. 18, 1974, entitled "Process and Apparatus for Astigmatic and Spherical Subjective Testing of the Eye" copending with this application and hereinafter incorporated by reference.

An advantage of this aspect of the invention of the specialized eye target incorporated with the direct patient input is that the eye, as there disclosed, can be made selectively sensitive to individual vision defects. Thus, a patient can adjust sphere, astigmatism and prism without specific inputs being interrelated. Thus, the patient adjustment at his hand wheel is limited in sensitivity to the particular component (for example, astigmatism) being tested.

Yet another advantage of this invention is that with the use of these specialized targets, astigmatism tests are isolated from sphere and vice versa. Thus, neither the examiner nor the patient has to adjust sphere to conform to astigmatism change, and astigmatism to conform to sphere change.

Yet another object of this invention is to disclose a gear box at the examiner's station which is capable of either routing patient input to optical elements being used to vary optical corrections, or alternately, enabling the examiner to specifically vary the optical corrections himself.

An advantage of this aspect is that the examiner can have normal adults in effect assist him in generating their own refractive corrections.

Yet another advantage is that where the person being tested is not capable of making his own adjustment — say, in the case of a juvenile — the examiner can adjust the optical elements himself.

Yet a further advantage of this invention is to enable the examiner to have two or more inputs focused simultaneously. For example, where bifocals are being prescribed, the spherical inputs can be simultaneously changed. Thus, for reading distance targets on middle-aged patients with reduced spherical accommodation, simultaneous change of sphere for both eyes can occur.

Other objects, features and advantages of this invention will become more apparent after referring to the following specification and attached drawings in which:

FIG. 1 is a perspective view of the eye test apparatus according to this invention illustrating the patient-projector eye paths as well as the patient-examiner eye paths with the patient input, the examiner's gear box (including examiner input and patient input routing) and the connection to the movable lens elements all being schematically shown;

FIG. 2 is a representative schematic sketch of a portion of the eye examiner's gear box illustrating a wheel for direct eye examiner input to the variable lens elements as well as the clutch mechanism for routing the patient input to an eye examiner's input wheel;

FIG. 3 is a schematic perspective view of the eye test device of this invention at the variable optic elements, the illustration schematically showing a target, a patient's eye viewing the target, the corrective optics intermediate the target and the patient's eye with schematically illustrated apparatus for varying the relative positions of the variable optic elements;

FIG. 4 is a view similar to FIG. 3 eliminating the linkages to the variable lens elements and illustrating a first spherical power adjustment used with this invention;

FIG. 5 is a view similar to FIG. 4 illustrating the determination of a first component of astigmatic correction used with this invention;

FIG. 6 is a view similar to FIG. 3 illustrating an angularly inclined new target (preferably at 45°) with the second and final spherical prescription change being made to determine the spherical correction required for the patient;

FIG. 7 is a view similar to FIG. 3 illustrating the determination of the final astigmatic component with the completion of the resultant test as to astigmatism and sphere for one eye;

FIG. 8 is a perspective view of a mechanism for determining prismatic correction to both eye paths of the patient; and, FIG. 9 is a perspective view of the reverse side of the mechanism for determining prismatic correction to both eye paths of the patient.

The reader should understand that the schematically shown eye test apparatus is disclosed in my William E. Humphrey U.S. Pat. No. 3,874,774 entitled "Eye Test Apparatus," which patent is incorporated herein by reference. This patient is abstracted as follows:

ABSTRACT

"An eye testing device for both subjective and objective testing of the eye is disclosed. Corrective optics having variable spherical and astigmatic inputs are placed at a location remote from a patient's eye. Intermediate the corrective optics and the patient's eyes focusing optics are placed. These focusing optics are preferably in the form of a field mirror. The focusing optics focus a real image of the corrective optics to the patient's eye. A projector projects a real image though the corrective optics to a specifically coherent real image location between the corrective optics and the patient. For subjective eye testing, the corrective optics are varied responsive to subjective patient visual acuity to provide the desired prescription. For objective eye testing, a projector acts as a light source typically projecting an image on the retina of the eye through and into an examiner-patient light path. The corrective optics — placed at the remote location between the examiner and projector on one hand, and the patient on the other hand — are varied responsive to the objective patient visual acuity, usually determined by conventional retinoscopic techniques. Thereafter with corrective optics prescribed, examination of the eye, exterior or interior, can occur through the patient-examiner eye path".

The claims of this U.S. Pat. No. 3,874,774 include claim 1 as follows:

CLAIM 1

"1. An eye testing device comprising: a patient viewing station; a projector, at least one light path between said patient viewing station and said projector; said projector including at least one target for projection and projecting optics for projecting at least one image to be viewed by a patient at a distance removed from said patient along said light path; corrective optics for emulating said patient's ophthalmological prescription for placement in said light path at a location between said projecting optics and said patient; focusing optics of preselected focal length removed by a distance greater than said focal length from said corrective optics toward said patient for focusing a real image of said corrective optics to the optical position of said patient's ophthalmological prescription proximate said patient's eye."

The reader will understand that FIG. 1, with the exception of the added material of patient hand wheel W, examiner gear box G, and examiner clutch L, is identical with FIG. 1 of my referenced U.S. Pat. No.

3,874,774 patent, the entirety of which I hereby incorporate by reference.

For the convenience of the reader, part of the text of my U.S. Pat. No. 3,874,774 follows with addition to emphasize the function of the patient hand wheel W, examiner gear box G, and examiner clutch levers L.

Referring to FIG. 1, a perspective view of the eye testing device of this instrument is illustrated. Typically, a patient P schematically shown by left eye 14 and right eye 15 is shown viewing focusing optics F. Focusing optics F retrodirect a light path to interocular drive I and to corrective optics C. Interocular drive I functions to adjust the instrument for variable patient interocular spacing.

Corrective optics C are shown in two locations. A first set of corrective optics lie between the patient P and a projector Q. Additionally, identical corrective optics C are located between the patient and the viewing examiner E. The viewing examiner E looks through examining optics O and interlopes at a beam-splitter B into the patient-projector eye path.

Patient P with his left eye 14 and right eye 15 views focusing optics F. Typically, the patient must be provided with a headrest or the like to maintain his eyes within given tolerances from the focusing optics F along the light path of the optical testing device. It should be understood that chin rests have deficiencies for this purpose as movement of the jaw in talking moves the eyes in viewing. Conventional headrests having headrest and bracing locations other than the chin will be sufficient to brace the patient for purposes of an examination.

A patient input wheel W is shown adjacent a schematically represented patient P. Wheel W is typically operated by the hand of the patient and affixed to the table or stand to which the eye test apparatus is mounted. Preferably, a flexible cable 201 takes the rotational output of the wheel W and routes it to the examiner gear box G.

At the examiner gear box G there are mounted eight examiner input wheels. These wheels include wheel 240 for controlling the sphere to patient left eye 14 at elements 40; wheel 241 for controlling the sphere to patient right eye 15 at elements 41; wheels 242 and 244 for controlling the astigmatism inputs to left eye 14 at elements 42 and 44; wheels 243 and 245 for controlling the astigmatic inputs to right eye 15 at elements 43 and 45; and, wheels 234 and 235 for controlling the base in, base out and base up, base down prismatic adjustments to the prism negative-positive pairs of lenses 34, 35.

Each of the examiner wheels has a corresponding clutch lever L. These wheels and corresponding clutch levers are: 242,342; 244,344; 240,340; 234,334; 235,335; 241,341; 243,343; and 245,345. By depressing the clutch lever L corresponding to each of the wheels of gear box G, the patient hand wheel W can be connected through the examiner input wheels to the respective corrective optics C as will hereinafter more fully be set forth. It is important to emphasize that this connection can be singular or in any combination. Thus, all of the examiner input wheels, some of the examiner input wheels, or one of the examiner input wheels can be connected to the patient input wheel W.

Projector Q is a projection apparatus. A light source 18 and light projecting optics 19, 20, 27 function together to project an image of a slide 25. Projecting optics 19, 20 and 21 are adjusted relative to slide 25 so as to project a rear image R, hereshown as the letter R to focus at a near infinite distance. As will hereinafter be more fully set forth, projector Q is completed at movable projecting lenses 34, 35.

Projector Q includes specially adapted optics for the eye testing device hereshown. Mirrors 27 and 28 are hereshown positioned to retrodirect the light path from projector 25. These mirrors are hereshown placed after lens elements 21 of the projector.

Secondly, the projected light from the projector Q passes through periscopes 30 and 31. Periscopes 30 and 31 respectively serve to project images for eyes 14 and 15 by splitting the image from the optics 22 into two separate paths, one path for each eye.

As required in conventional eye testing optics, the light paths must be compensated for traditional "wall-eye" or "cross-eye" corrections. Accordingly, relatively movable projection lenses 34 and 35 are shown in each of the light paths to patient eyes 14 and 15 respectively.

As will hereinafter be explained in more detail with reference to FIGS. 8 and 9, vertical and horizontal movement of the projection lenses 34, 35 will generate prismatic elements necessary for binocular prismatic prescription.

Corrective optics C are illustrated in two locations. For the purposes of a preliminary understanding of this invention, the corrective optics C in the projector Q-patient P light path will first be discussed. Beam-splitter B and interocular drive I will both be ignored with stress only being given to focusing optics F. Thereafter, and with reference to the patient P-examiner E light path, the functon of interocular drive I and beam-splitting optics B will both be set forth in summary.

Corrective optics C consists of relatively movable variable focal length or variable spherical optics 40 for the eye path of patient eye 14 and relatively movable variable focal length or variable spherical optics 41 for the eye path of patient eye 15. both of these optics consist of paired variable focal length lenses which move relative to one another to achieve the desired spherical correction necessary to prescribe for the patient. Such paired countermoving optical elements are fully described and set forth in the Luis W. Alvarez U.S. Pat. No. 3,305,294 entitled "Two-Element Variable-Power Spherical Lens", and the Luis W. Alvarez and William E. Humphrey U.S. Pat. No. 3,507,565 entitled "Variable-Power Lens and System."

Additionally, astigmatic inputs for correction of patient P astigmatism are required. These astigmatic inputs occur at relatively movable lens pairs 42 and 44 for eye 14, and 43 and 45 for eye 15. The configuration of each of the pairs of lens optics 42–45 as well as the effect of correction which occurs upon lens relative movement is fully described in William E. Humphrey U.S. Pat. NO. 3,751,138 entitled "Variable Anamorphic Lens and Method for Construction Lens."

One comment can be made about the astigmatism generated by variable astigmatic lens pairs 42 and 43 on one hand, and 44 and 45 on the other hand. Typically these variable astigmatic lenses are selected so that variable astigmatic lens pairs 42 and 44, for example, generate astigmatism along rotational alignments 45° one from another. Thus, by relative movement of the lens pairs of each of the elements 42–45, virtually all optically practical astigmatic prescriptions can be generated.

Seeing the placement of the corrective optics C, the mechanism for effecting their relative movement to procure continuously variable optic prescription in sphere and astigmatism can now be set forth. First, and referring to FIGS. 2 and 3, the function of examiner wheel 240 in a portion of gear G will be shown as varying the relative spacing of variable spherical lens elements 40. Thereafter, the depression of clutch levers L to couple the movement of wheel 240 to the patient's hand wheel W through depression of lever 340 will be set forth. In understanding the following explanation, the reader will understand that the movement of wheel 240 to effect relative movement of the lens elements 40 and the coupling of the patient's hand wheel W to wheel 240 is typical. All of the remaining examiner input wheels and clutch levers L work in a precise analogous fashion.

Wheel 240 is rotatably mounted on a horizontal axis shown at 200. This wheel for only a portion of its periphery, in the vicinity of 201, extends above the bracket 205 to which the wheel is rotatably mounted.

The periphery of wheel 240 is provided with a series of gear teeth 207. Teeth 207 serve as a convenient surface for the examiner to manipulate the wheel as well as a surface to which gearing interior of the gear box G can mesh as will hereinafter be made more fully apparent.

One side of the wheel is provided with a spiral cam 209. As can be seen, groove 209 expands radially outward counterclockwise over 360° of wheel rotation from axis 200 of examiner input wheel 240.

Likewise, and on the opposite side of wheel 240, a spiral cam 210 is placed in wheel 240. Spiral cam 210 expands radially outward clockwise over 360° of wheel rotation from axis 200 of examiner input wheel 240.

Each of the cams 209, 210 moves out at the same rate with respect to the rotation of wheel 240. It will thereby be understood that upon clockwise rotation of wheel 240, follower $A_1$ for cam 209 moves away from axis 200 at the same rate with respect to wheel 240 as follower $A_2$ for cam 210 moves toward axis 200 of wheel 240.

The movement of the cam followers $A_1$ and $A_2$ on either side of wheel 240 can be easily understood. First, construction of the cam followers will be described together with their connection to control cables K. Thereafter, and with respect to FIG. 3, the function of the control cables K in introducing variable movement of the lens elements 40 will be set forth.

Cam follower $A_1$ has a rod 211 connected centrally to axis 200 at one end, and passed through a holding block 212 at the opposite end. The function of rod 211 is to provide a surface over which the cam follower $A_1$ can ride radially of wheel 240 towards and away from axis 200. A pawl 214 rides interior of the groove 209. Thus, when wheel 240 is rotated, cam follower $A_1$ at pawl 214 rides radially of the wheel 240 on the rod 211. It should be understood that cam follower $A_2$ is precisely analogous. It has its own pawl that rides interiorly of cam 210.

It will be seen when follower $A_2$ is in a disposition extended away from axis 200, follower $A_1$ is radially towards axis 200. With clockwise rotational movement of wheel 240, the rate of movement of follower $A_1$ away from axis 200 is the same as the rate of movement of follower $A_2$ towards axis 200. As will hereinafter be made more apparent, this enables precise movement of the controlled variable optical elements 40 relative to the viewer eye path.

Each of the cam followers at a cable clamp 216 grips the interior of a cable 218. This cable is of the sheath-bicycle cable variety with the cable sheath 219 being fastened to the follower support 212 and the interior cable reciprocally movable in sheath 219.

Turning now to FIG. 3, production of the variable movement of the lens elements 40 can be readily understood. As can be seen, the control cables $K_1$ and $K_2$ attach to each of the pairs of the relatively movable, variable, spherical optics 40. When cable $K_1$ expands outwardly, cable $K_2$ retracts inwardly. As the cables are looped around a pulley 220, relative movement of the lens elements 40A, 40B easily occurs.

With brief reference to FIG. 1, it will be remembered that the patient's hand wheel W through a rotational flex cable 201 has an output to the gear box G. This output is channeled into shaft 221. Shaft 221 extends the substantial width of the gear box G and has permanently attached to it a series of gears including gear 222 corresponding to wheel 240.

A second gear 224 is rotatable relative to shaft 221. This gear has an outer periphery similar to the periphery of gear 222. Inwardly it is provided with a smaller reduction gear 226. As is plainly illustrated, gear 226 rides on the geared periphery 207 of wheel 240. Thus, when the wheel 240 rotates clockwise, gear 224 likewise rotates counterclockwise.

The function of clutch lever L at button 340 can now be understood. Typically, button 340 connects to a spring-biased lever 227 rotatable about an axis 228. The bias provided to lever 227 is upwardly and away from the gears 222, 224.

Overlying each of the gears 222, 224, lever 227 has mounted thereto meshing gear 229. Preferably, this gear is sized in spacing of the teeth to mate with the corresponding gear teeth of gears 222, 224. Gear 222 and 224 may have differing diameters. This difference assures mesh upon small relative rotation of meshing gear 229 with each of the gears 222 and 224.

When button 340 is depressed, spring-biased lever 227 pivots on axis 228 until meshing gear 229 contacts the side-by-side teeth of gears 222, 224. Simultaneously, rotation of gears 222, 224 occurs. Thus, rotation of wheel 240 is geared to rotation of the patient's hand wheel W through the rotation flex shaft 201.

Since the detail illustrated in FIG. 2 is typical for all eight gears shown, it will be immediately understood that depressing any of the levers L for the respective examiner input wheels will cause patient hand wheel W to be connected either singularly or together with any input that the examiner selects. For example, where the sphere in both patient's eye paths is to be varied together (for example, in obtaining simultaneous variation of sphere in both eye paths with adults having lost spherical accommodation), the patient hand wheel W can vary both spheres.

It is preferable with the apparatus here shown to provide for an electronic readout of the prescription. See my co-pending U.S. Pat. application Ser. No. 483,171, filed June 26, 1974, entitled "Apparatus for Ophthalmological Prescription Readout," now U.S. Pat. No. 3,927,933, issued Dec. 23, 1975. To this end, a spiral potentiometer 230 connected at a gear 231 to the periphery of wheel 240 is provided. Leads from this spiral potentiometer can be connected to such automated readout apparatus.

Focusing optics F function to focus a real image of the corrective optics C to the eyes 14 and 15 of patient P. Stated in other terms, the real image R projected by the projector Q through the corrective optics C is the same as if the corrective optics C were removed from their location in the projector light path and placed immediately in front of eyes 14 and 15 of patient P.

Focusing optics F required for projecting a real image of the corrective optics C to the eyes 14 and 15 of patient P are here shown in the form of field mirror 50. It should be understood that a conventional lens or lenses which accomplish this function could as well be employed in this invention. However, the focusing optics F here shown in the form of field mirror 50 are particularly preferred.

There is a cylinder effect or astigmatic effect of mirror 50 due to the increasing angle of incidence or angle of reflection to or from mirror 50. Mirror 50 can be manufactured with an aspherical surface to correct this astigmatic input. More efficiently, mirror 50 can be elastically deformed by bar 70 and brackets 72. Specifically, and where the eyes of patient P directly overlie mirrors 60 and 61 of interocular drive I, an aspheric astigmatic correction can be elastically made to mirror 50 by pulling in at brackets 72 at the top of field mirror 50 and pushing outwardly on the sides of field mirror 50 at bar 70.

Returning to a brief description of the reflective properties of interocular drive I, it will be noted that the light path from eye 14 of patient P impinges upon field mirror 50, mirrors 60 and 62 of interocular drive I to relatively moving lens pairs 40, 42 and 44. Similarly, the light path from eye 15 of patient P impinges upon field mirror 50, mirrors 61 and 63 of interocular drive I and corrective optics relatively moving lens pairs 41, 43 and 45. Thus, independent adjustments to the corrective optics at relatively moving lens pairs 40, 42 and 44 all produce corrections to eye 14 of patient P. Similarly, independent adjustments to relatively moving lens pairs 41, 43 and 45 all produce corrections to eye 15 of patient P.

It will be remembered and understood that each of the relatively movable lens pairs are adjusted independently. Thus, by turning the corresponding examiner input wheel or the patient hand wheel W linked through a gear lever L to an examiner input wheel, independent adjustment of the corrective optic elements occurs.

Correctice optics C must lie between the real image R of projector Q and the slide of image R which is projected. Location of the corrective optics C at either the real image R, or at the slide in the projector Q will not be operative.

Understanding this much of the invention set forth, and ignoring beam-splitter B and the observing light path O to examiner E, a subjective refraction of patient P can now be discussed.

Basically, patient P is asked to look at the real image R in the vicinity of focusing optics F. Thereafter, spherical correction is made by relative movement of the variable lens pairs 40 for patient eye 14, and 41 for patient eye 15 until optimum vision of the real image R occurs. Thereafter, astigmatic input can be made by sequential relative movement of relatively moving variable lens pairs 42 and 44 for the left eye 14 of patient P, and relatively moving lens pairs 43 and 45 for the right eye 15 of patient P.

Typically, the lens sequence of operations of relatively moving lens pairs 40, 42 and 44 will be repeated twice to obtain an optimum refraction for patient eye 14. Similar repeat of the sequence of operations of adjustment of relatively moving lens pairs 41, 43 and 45 will be made to achieve adjustment for eye 15.

It will be understood by those skilled in the art that dependent upon the magnification of the focusing optics F hereshown as field mirror 50, the amount of correction actually placed into the corrective optics C will provide a different effective correction to the patient P at the patient viewing station. Usually the instrument will be constructed for unit magnification. In these circumstances, the diopter correction applied at the corrective optics C will relate closely to the effective diopter correction that the patient views.

Where, however, the effective magnification of the focusing optics is other than unity, the diopter correction for the patient Dp is related to the diopter correction at the corrective optics Dc as follows: $Dp = Dc(M^2)$ where $M$ is the ratio of the focusing optics (field mirror) to corrective optics distance over the focusing optics to patient eye distance.

It has heretofore been emphasized that patient hand wheel W has particular utility when used in combination with specialized targets. Such targets are disclosed in my co-pending U.S. Pat. application Ser. No. 452,232, filed Mar. 18, 1974, entitled "Process and Apparatus for Astigmatic and Spherical Subjective Testing of the Eye", now U.S. Pat. No. 3,947,097, issued Mar. 39, 1976. This patent, which is hereby incorpoated by reference, is abstracted as follows:

ABSTRACT OF THE DISCLOSURE

"An apparatus and process for determining subjective astigmatic and spherical prescription for the eye is disclosed. A target, consisting of a straight line, is focused for maximum clarity by the adjustment of spherical optics, causing the line to become proximate to the retinal viewing plane of the eye. Change of astigmatic correction is made along at least one axis diagonal to the line until maximum sharpness of the line results, without resultant spherical change and resultant movement of the image away from the retinal plane of the eye being tested. A second target, again consisting of a straight line, is introduced; this line target is angularly inclined to the first target, preferably at 45°. Spherical adjustment is made to obtain subjective line sharpness. Change of astigmatic correction is made along at least one axis diagonal to the line until maximum sharpness of the line results, without resultant spherical change and resultant movement of the image away from the retinal plane of the eye. By the expedient of vector analysis of the two astigmatic components, astigmatic correction can either be plotted on Cartesian coordinates (in accordance with a technique recently developed), or conversion to the more conventional polar description of astigmatism using cylinder power and rotation can occur. A specialized line target consisting of a three point source smeared by the superimposition of strong cylinder in the range of 4 to 12 diopters is disclosed. This specialized target, when the point sources are arrayed in a triangular configuration, can be adjusted using patient Vernier visual acuity, a visual acuity common to a high degree in large numbers of the population."

The claims of this patent application include claim 1 as follows:

"1. A process for determining optometric prescription for the eye including the steps of: providing a patient viewing station; providing at least one first straight line target of first arbitrary preselected angular alignment without regard to any suspected principle axis of the patient to a view path from said patient viewing station; providing in said view path variable spherical optics to vary the spherical correction of said target as viewed by said patient; varying the spherical correction responsive to subjective patient visual acuity of said first straight line target; providing in said view path first variable astigmatic optics for varying astigmatic lens power along said first intersecting diagonals at substantially equal and opposite angles from the preselected angular alignment of said first straight line target; said first variable astigmatic optics varying said astigmatic power from positive to negative along one axis of said first intersecting diagonals and from negative to positive along the other axis of said first intersecting diagonals; and, varying the first variable astigmatic optics responsive to subjective patient visual acuity of said first target to obtain a first component of astigmatic prescription for said patient."

The reader will understand that FIGS. 3, 4, 5, 6 and 7, with the exception of the schematically shown patient hand wheel W, cable $K_1$, cable $K_2$, etc. and examiner input wheels, are substantially identical to the respective FIGS. 1, 2, 3, 4 and 5 of U.S. Pat. No. 3,947,097. Only the numeric designations have been changed to avoid confusion with other numerals appearing herein.

For the convenience of the reader the disclosure of my U.S. Pat. No. 3,947,097 is summarized below in the following specification with the exception that the function of the patient hand wheel W, the examiner gear box G, and clutch lever L is interdispersed to enhance understanding of the present invention.

Referring to FIG. 3, a schematic diagram in partial perspective illustrating the patient P eye path for left eye 14 is shown. For simplicity, the eye path is shown absent focusing optics F, interocular drive I, beamsplitter B, and projector Q. Likewise, the path to examiner E has been omitted.

Viewing the perspective and schematic view from left to right, a target $R_1$ consisting of a straight line is first illustrated. Typically, straight line is a line of one minute of arc or less to the patient's eye (this dimension being at the minimum of visual acuity of the eye) although coarser targets may also be useful. The target $R_1$ can be generated in any number of conventional ways, from the conventional eye chart to projectors and the like.

The patient P, schematically illustrated at eye 14, views target $R_1$ through corrective optics. Responsive to his visual clarity of the target $R_1$ being viewed, adjustment is sequentially made to the spherical optic lens pairs 40 (for the first time), the first astigmatic power lens pair 42, the spherical optic lens pairs 40 (for the second time), and finally to the second astigmatic power lens pair 44.

Regarding lens pairs 40, 42 and 44, the reader should realize that these are extremely complex optical surfaces. These extremely complex surfaces are here schematically shown as flat pieces of glass. Their complex surfaces can only be understood after referring to the referenced U.S. Pat. Nos. 3,305,294; 3,507,565; and 3,751,138.

Broadly, first astigmatic optic lens pairs 42 are moved relatively one to the other responsive to objective patient manifestations of visual acuity of target $R_1$. First astigmatic lens pairs 42 change the astigmatic power or focal length from positive to negative along one diagonal and simultaneously change the astigmatic lens power from negative to positive along the remaining diagonal. Opposite relative horizontal movement produces opposite astigmatic adjustments.

Likewise, second astigmatic lens pairs 44 are moved relatively one to the other responsive to objective patient manifestations of visual acuitry of target $R_1$. Second astigmatic optics 44 change the astigmatic power or focal length from positive to negative along the vertical axis and simultaneously from negative to positive along the horizontal axis upon relative movement of each of the lenses of the lens pairs in relative horizontal movement. Opposite relative horizontal movement produces opposite astigmatic adjustments.

Before proceeding further with the description of this invention, one aspect of the first embodiment illustrated in FIGS. 3–7 should be made clear. The variable astigmatic lens element pairs 42 and 44 are of the type that produce perpendicularly crossed positive and negative astigmatic lens power along axes normal one to another. While the lens elements here illustrated are preferred, it is apparent that other lenses and optic apparatus could be used for generation of this effect. For example, see my co-pending U.S. Patent application Ser. No. 263,329, filed June 15, 1972, entitled "Ophthalmological Apparatus and Process Having Independent Astigmatic and Spherical Inputs", now U.S. Pat. No. 3,822,932, issued July 9, 1974.

Having set forth the mechanics of this invention, operation of the process and apparatus for the generation of the subjective eye test of this invention can now be understood by first understanding optical limitations relating to astigmatism.

First, it will be well to emphasize why only straight line targets consisting of preferably a single straight line or at least a plurality of parallel straight lines are used.

Referring to FIG. 3, it will be noted that target $R_1$ is shown as a single straight line of exaggerated width extending in the vertical direction. An imaginary line 424, shown in broken horizontally extending lines, is also shown. Focus of these lines relative to the imaginary and schematically shown retinal plane 426 of eye 14 of patient P will help to understand the function of the variable astigmatic lens pairs 42 and 44 of this invention.

Assume that the eye 14 of the patient P has an appreciable astigmatic aberration. It is in the nature of astigmatism that straight lines of certain orientations will focus at different distances relative to retinal plane 426 of eye 14. In the view hereshown, the aberration of the patient P causes the imaginary horizontal line 424 to focus behind the imaginary retinal plane 426 and the vertical straight line $R_1$ to focus in front of the imaginary retinal plane.

Clearly, if the corrected astigmatic view is to be made of either the line targets $R_1$ or 424, differing spherical corrections will be required to bring into focus and view either of the line targets $R_1$ or 424. Understanding this, it should be doubly clear that the spoke-like multilined targets of the prior art cannot be satisfactorily used with this invention. As different lines of different angular orientation have different planes of best focus in the vicinity of the retinal plane 426 of a patient P having astigmatism, affording completely different patient viewing, only line targets having parallel lines can be satisfactorily used.

Second, once a straight line target, such as straight line target $R_1$, is focused to the focal length of an eye 14 having astigmatic aberration, astigmatic adjustment should be made along a plane that will not cause relative movement of the focal length of the viewed line with respect to the retinal viewing plane of the eye. Stated in other terms, astigmatism power adjustments should be made along normally disposed axes in equal positive and negative powers on each respective axis, these normally disposed axes being substantially 45° from the angle of the target. Thus, astigmatic correction in such a component can be made without affecting the overall focal length of the astigmatism target.

Having these precepts explained and understood, the basic manipulative process of this invention can be explained with sequential reference being made to FIGS. 3–7 of the drawings.

Referring to FIG. 3, patient P is asked to view line $R_1$. Thereafter, relative movement of the spherical lens elements 40 is made responsive to maximum or optimum visual acuity of line $R_1$. Movement of the line to coincidence with the retinal plane 426 of the patient P results as is illustrated in FIG. 4.

Typically, such movement occurs in one of two manners. First, the examiner can move wheel 240 to vary prescription and conduct a "see better - see worse" inquiry. Second, and by examiner depression of lever 340, direct linkage of patient hand wheel W to wheel 240 can occur. Patient movement of optical elements 40 results. This movement is made to optimize the patient optical correction.

When this movement is optimized and is shown in the extreme right of FIG. 4, line $R_1$ does not appear with its full optical clarity. This is because the ambient astigmatism of the patient P along diagonals relative to straight line $R_1$ causes the edges thereof to be blurred. It therefore remains to correct these astigmatism aberrations without causing resultant spherically related movement of line $R_1$ out of the retinal plane 426.

Referring to FIG. 5, second astigmatic lens pairs 42 have been moved relative to one another to cause optimum visual sharpness to patient P. This movement occurs at examiner input wheel 242 and on patient input wheel W through lever 342. Since second astigmatic lens pairs produce correspondent negative and positive or positive and negative astigmatic lens power along perpendicular axis — each of which is diagonal to vertical straight line target $R_1$ — subjective improvement of the visual acuity of line target $R_1$ results without any change in the focal length. This adjustment produces the final astigmatic prescription for one component of astigmatism (the only qualification being that it may be desirable to repeat the entire sequence herein to optimize the optical settings).

Referring to FIG. 6, a new line target $R_2$ has been placed for patient viewing. Preferably, this line target should be at an altered alignment of 45° with respect to the patient P. It should be noted, however, that precise 45° alignment change of the target is not required. Changes in target alignment of more than 30° can produce tolerable results.

Referring to FIG. 6 and remembering the sequence of FIGS. 3–5, it will be remembered the astigmatic aberration of eye 14 of patient P will cause the new line target $R_2$ to have a differential focal length with respect to the imaginary retinal focal plane 426 of eye 14. Therefore, a second spherical correction will be made at spherical lens pairs 40. This adjustment will be made responsive to maximum patient visual acuity of new line target $R_2$ and will cause the focal impingement of the line target $R_2$ to fall on the retinal plane 426. As before, movement will be made either by the examiner at examiner input wheel 240 or through patient hand wheel W by examiner depression of lever 340.

A surprising result occurs at this juncture of the process of this invention. The second adjustment of sphere to coincide straight line target $R_2$ with retinal plane 426 causes the final spherical power to be known. This occurs even though the final astigmatic component is not known. Moreover, determination of the final astigmatic component will not effect the final spherical setting of the illustrated instrumentation, although transformation of the prescriptions obtained herein to the more accepted prior art prescription will result in the adjustment of sphere merely because of the presence of the changing cylinder.

It should be remembered with respect to FIG. 6, that spherically optimizing the view of straight line target $R_2$ leaves visual astigmatic clarity yet to be obtained. Stated in other words, patient P at eye 14 does not get the optimum clarity of his view line $R_2$ because of the presence of the uncorrected astigmatic horizontal and vertical astigmatic components.

Referring to FIG. 7, first astigmatic optic lens pairs 44 are translated one to another responsive to maximum visual acuity. This translation occurs either by the manipulation of examiner input wheel 244 or through manipulation of patient hand wheel W through depression of lever 344. The final component of astigmatism is obtained. Again, since the respective negative and positive or positive and negative axes of astigmatic power adjustment are at substantial 45° alignment to straight line target R, no resultant movement off of the retinal plane 426 is induced. Moreover, this adjustment is the final adjustment in the process of this invention giving the final coordinate of the desired astigmatic prescription.

Having explained the process of this invention, it should be made clear that the sequence of steps herein set forth can be repeated. This may be done to optimize the prescription obtained or alternately to check prescription accuracy.

It should also be understood that the physical positioning of lens pairs 40, 42 and 44 may be permuted, if desired, without invalidating the procedure.

It should be noted that each line target $R_1$ of FIGS. 3–5 and $R_2$ of FIGS. 6 and 7 requires adjustment of only two, and never three optical components. Thus, for target $R_1$, only spherical optics 40 and first astigmatic optics 42 are adjusted; second astigmatic optics 44 are not adjusted.

Likewise for target $R_2$, only spherical optics 40 and second astigmatic optics 44 are adjusted; first astigmatic optics 42 are not adjusted.

It should also be appreciated that for each target, it does not make any difference in what order adjustment occurs. The spherical optics can be adjusted prior to the adjustment of the applicable astigmatic optics. Conversely, the applicable astigmatic optics can be adjusted prior to the adjustment of the spherical optics.

It is surprising to note that in the manipulation of either the spherical optics 40 or the astigmatic optics 44 for target $R_2$, the final prescription results. This is true whether spherical optics 40 are first manipulated, or astigmatic optics 44 are first manipulated.

It will be understood that my U.S. Patent application Ser. No. 452,232, filed Mar. 18, 1974, entitled "Process and Apparatus for Astigmatic and Spherical Subjective Testing of the Eye," now U.S. Pat. No. 3,947,097, issued Mar. 30, 1976, discloses alternate test procedure using an optical smearing of a point source through the interposition of a strong cylindrical lens. Those skilled in the art will appreciate that the test procedure there used could as well be used here.

Having set forth the function of this instrument to provide a subjective refraction, attention can now be given to the examiner-patient light path. Typically, the examiner-patient light path is detoured at a beam-splitter B. It will be observed that the detour of beam-splitter B is between corrective optics C at lenses 40–45 and the patient P. There is an important reason for this placement.

It has been found that the relatively intense light of projector Q when projected through corrective optics C causes many reflections at the air-glass interfaces provided by the relatively moving optics of lens pairs 40–45. Ideally, these reflections from the relatively moving lens pairs should not be reflected into the examiner-patient light path. Therefore, by the placement of beam-splitter B between the corrective optics C and the patient P, all reflections of the corrective optics C relative to projector Q will pass into the projector Q light path and not the examiner E light path.

Beam-splitter B functions to divide out light from the projector Q. It has been found useful to provide a beam-splitter composed of a fully reflective surface with one or more small apertures in the reflective surface through which illumination may be passed to the patient P while return light is collected from the fully reflective area. In this way, the optics may be adjusted so that the small apertures lie reimaged in the plane of the cornea, and the corneal reflection is, in turn, reflected to the area of small apertures, and hence only poorly reflected into the optical path of examiner E.

To provide an objective eye examination of patient P it is necessary that the examiner E look through corrective optics C, which corrective optics C are identical to those corrective optics through which projector Q projects the real image R. Accordingly on each side of beam-splitter B there are provided identical relatively moving variable lens pairs corresponding to each of the variable lens pairs previously described.

It is not intended to exclude the possibility of placing the beam-splitter between a single corrective optics C and projector Q; however, present day antireflective coatings are not sufficiently effective to provide as high a quality result as the approach hereshown.

Take the case of eye 14 and variable spherical optics 40, and variable astigmatic optics 42 and 44. Typically, variable spherical optics 46 identical to variable spherical optics 40 are provided. Similarly, variable astigmatic optics 48 identical to variable astigmatic optics 42 are provided. Finally, variable astigmatic optics 52 identical to variable astigmatic optics 44 are provided.

It will be remembered that each of the varible lens pairs comprises two pieces of relatively moving optical material such as glass which generate the variable lens effect, be it astigmatism or conventional spherical lens correction. Accordingly, it is desirable to use identical lens elements for each of the correspondent pairs of optics above mentioned. Furthermore, it is desirable to produce precisely identical relative movement between the relatively moving lens pairs.

Precisely identical lens movement must occur between the relatively moving pieces of glass of lens pairs 40 and the relatively moving pieces of glass of lens pairs 46. Similarly, precisely identical lens movement between the relatively moving pieces of glass pairs 42 must be identical to the movement of the pieces of lens pairs 48. Finally, precisely identical movement between the pieces of glass of lens pairs 44 must be identical to the relative movement of the pieces of glass of lens pairs 52.

Regarding the mechanical connections between the respective lens elements 40,46; 42,48; 44,52; 41,47; 43,49; and 45,53; it should be understood that brackets shaped in the form of a letter L substantially as shown in my incorporated U.S. Pat. No. 3,874,774 can be used. In such brackets, each pair of correspondent lens elements for each eye are moved together. For example, the separate lens elements of lens pairs 40 and 46 would be movable together by an identical and precisely analogous amount.

Returning to the description of the patient P-examiner E light path, the light path diverted by beam-splitter B and passing through examiner corrective optics C proceeds typically through apertures 90 and 91. Apertures 90 and 91 are radially equidistant from a shaft 93 about which periscope optics 95 revolve. As is apparent, registry of the inlet of periscope 95 with aperture 90 will allow the examiner E to interlope on the light path to patient's eye 14. Similarly, registry of the inlet of periscope 95 with aperture 91 will allow the examiner E to interlope on the light path to patient's eye 15.

After passing through periscope optics 95, light is diverted upwardly to prism 96 and eyepiece 98 to examiner E. Examiner E can thus observe either eye 14 or eye 15 of patient P.

The examiner will wish to separate views of each of the respective eyses of patient P. Typically for biomicroscopy and ophthalmoscopy, where examination of the various interior layers of the eye such as the retina are conducted, the image of the patient's eye produced for examiner E must be relatively closer to the examiner E. For this purpose a conventional Bertrand lens assembly 100 is mounted about a pivot 101 and moved into the examiner E-patient P light path.

Additionally, and for examination of the exterior of the eye such as that required for retinoscopy, keratometry and biomicroscopy on the various exterior layers of the eye, Bertrand lens assembly 100 will be rotated about pivot 101 out of the examiner E-patient P light path.

Having set forth the examiner-patient optics from beam-splitter B to examiner E, attention can now be directed to the interocular drive I.

Interocular drive I includes first and second relatively moving racks 64 and 65. Rack 64 rigidly mounts mirrors 60–62 from the light path 14 of patient P. Rack 65 rigidly mounts mirrors 61–63 from the light path from patient's eye 15.

Those skilled in eye examination art are well aware of the physical fact that the interocular spacing for different patients varies between relatively wide limits. In the design of this optical instrument, it has been found that the interocular spacing for both projector Q and examiner E must be the same. Thus, the instrument must accommodate the variable ocular spacing of the eyes 14 and 15 on one hand, and yet project from the interocular drive towards examiner E or projector Q a constant ocular spacing typically in the order of 10 cm.

Mirrors 60 and 62 on one hand, and 61 and 63 on the other hand, are hereshown as roof mirrors. It has been found that by counterrelative and transverse movement of racks 64 and 65 provided by a pinion 67 and a drive 68, individual adjustment transverse of the light path of the roof mirrors can occur. This transverse adjustment preserves the same length of light path, provides for a variably spaced input to interocular drive I from patient P, and at the same time produces an identically spaced parallel light output from interocular drive I to projector Q and examiner E.

Interocular drive I has an additional function. It will be remembered that the function of focusing optics F was to focus a real image of the corrective optics C to the eyes of the patient P. Typically, the real image of the corrective optics C can be at two locations. The first location is the conventional eyeglass location on the bridge of a patient's nose. The second location is the conventional contact lens location on the cornea of the patient's P eyes 14 and 15. Other locations may be preferred for certain tests such as ophthalmoscopy where the beam splitter may be imaged at the cornea.

The amount of adjustment of the interocular drive towards and away from the patient to produce corresponding shift of the image of the corrective optics at the patient can be readily understood. The resulting shift of the corrective optics can be described by the formula $D = 2/M^2 S$ where S equals the shift of the interocular drive towards and away from the patient; M is the ratio of the field mirror to corrective optics over the field mirror to eye distance along a central ray; and, D is the amount of effective correction optics shift.

Interocular drive I is movable towards and away from patient P. In movement towards patient P, the optical path between corrective optics C and focusing optics F is lengthened. Movement of the real image of the corrective optics C away from the cornea of patient's eyes 14 and 15 occurs.

Similarly, movement of interocular drive I away from patient P shortens the light path. Movement of the real image of the corrective optics C to an eyeglass location at the cornea results. It has been found that movement of the interocular drive I towards and away from patient P can be easily affected by a drive 120.

It should be realized that other expedients can result in the apparent movement of the corrective optics C relative to patient P. For example, actual movement of corrective optic C or focusing optic F, while not as desirable, can suffice to produce this apparent movement of the real image of corrective optic C to the eyes of the viewer.

Referring to FIGS. 8 and 9, apparatus for adjusting the prismatic prescription of the patient is illustrated. A plate 500 is shown having two apertures 503 and 515. Aperture 503 surrounds the eye paths from patient left eye 14 to the projector. Likewise, aperture 515 surrounds the aperture from patient's right eye 15 to the projector.

Over each of the apertures there is mounted a movable lens within a rectangular frame. These lenses, lens 34 in frame 504 and lens 35 in frame 505, are movable.

Lenses 34 and 35 serve two purposes. First, and when the lenses are in any position, they serve as the projection lenses to each of the eye paths to eyes 14 and 15. Second, when the lenses move, they introduce prism. When they move towards and away from one another in the horizontal direction, lenses 34 and 35 produce prism in the horizontal direction. When these same lenses 34, 35 move towards and way from each other in the vertical direction, they produce prism vertically. Obviously by the combination of prism movement, a component of prismatic prescription in any direction can result. In explaining the prismatic movement of the projecting lenses 34, 35, their horizontal relative movement will first be set forth with respect to FIG. 8. Thereafter, and with respect to FIG. 9, vertical relative movement will be set forth Each of the frames 504 and 505 fasten to respective vertical posts 506 and 507. This occurs at vertical journals 508 and 509 in the upper and lower portions of the outside of the frames 504, 505.

Posts 506, 507 are in turn fastened to a horizontally traveling bar 510, 511. Bar 510 slides on a shaft 512 at horizontal journals 514; bar 511 slides on a shaft 513 at horizontal journals 516.

It is necessary to prevent rotation of the frames 504, 505 about their respective shafts 506, 507. To this end, a pawl 520 fits into a capturing indentation 522 in frame 504 and a corresponding pawl 521 fits into a corresponding indentation 523 in frame 505.

It will be remembered with respect to the description of FIG. 2 that each wheel includes cables. It will be remembered, for example, that wheel 235 has a dual cable output which is here shown as cables K3 and K4. These respective cable outputs are routed around pulley 550 and the cables attached to the pulley at attachment 551.

Pulley 550 is a reduction pulley. It has a reduced inner diameter 552 and endless cable 549 fastened at point 553 on reduced inner diameter 552. Cable 549 forms an endless loop around and between two side pulleys 554 and 555. Frame 504 is attached to the forward run of the endless cable 549 at 556; frame 505 is attached to the rearward run of endless cable 549 at 557.

The bottom of the respective lens frames 504 and 505 is supported on respective wheels 560 and 561. These wheels are journaled at the outboard end of an inverted T-shaped bar 562. This bar is journaled to plate 500 at pivot 563. Inverted T-shaped bar 562 extends through to the back side of the plate at 564 through an aperture 56.

Movement of the projecting lenses 34, 35 with respective cable movement of cables K3 and K4 can now be easily understood. Assuming that cable K3 is gathered to wheel 235 and K4 is played out from wheel 235, pulley 550 will rotate counterclockwise. Cable 549 wound around reduction pulley 552 will at its rearward strand at the left side of FIG. 8 be gathered and on the rearward strand at the right side of FIG. 8 be played out. The lens frames 504 and 505 will move away one from another. Opposite movement of cables K3 and K4 will produce opposite lens frame movement. Lens frames 504 and 505 will move towards one another.

When the lenses 34,35 move away from one another, a base out prism will be introduced. Likewise, when the lenses move towards each other a base in prism will be introduced which deviates the viewing path outwardly.

Vertical movement of the paired lenses can be easily understood with reference to FIG. 9. It will be remembered that FIG. 9 is a view from the reverse side of the assembly as shown in FIG. 8.

Cables K5 and K6 emanate from examiner input wheel 234. These cables are wound around a reduction pulley 573 and attached to the pulley at point 574.

Similar to reduction pulley 550, reduction pulley 573 has an inner pulley 575. This pulley has fastened thereto at point 576 an endless cable 577. This cable in turn loops around two end pulleys 578, 579. The lower run of the endless cable 577 is fastened to inverted T-shaped bar 562 at point 564 on the reverse side of the plate 500.

Assuming that cable K6 is gathered to examiner input wheel 234 and cable K5 played out from examiner input wheel 234, counterclockwise movement of the pulley 573 will occur. The lower run of cable 577 will move to the left, as shown in FIG. 9.

Upon such movement to the left, lens 34 will rise and right lens 35 will fall. A base up prism will be introduced in the view path of eye 14; a base down prism will be introduced in the view path of eye 15. Opposite cable movement will produce an opposite result.

It should be understood that this invention sets forth the prefered embodiment of my optical instrument. It should be realized that variations can easily occur. For example, the field mirror configuration of the preferred embodiment is not required. Moreover, the continuously variable lenses here shown are not required for the practice of this invention. For example, the crossed cylinder shown in FIGS. 1 and 2 of my U.S. Pat. No. 3,822,932, issued July 9, 1974, entitled "Optometric Apparatus and Process Having Independent Astigmatic and Spherical Inputs," could just as well be used. Likewise, other modifications can occur without departure from the spirit and scope of this invention.

I claim:

1. An eye testing apparatus including in combination a patient viewing station for testing at least one eye of a patient; a target for view by said patient located along at least one view path for one eye; first correction optics in said view path between said patient viewing station and said target, said first corrective optics including first variable spherical optics to vary the spherical correction of said target and first variable astigmatic optics to vary the astigmatic correction of said target; first means for varying said first variable spherical optics responsive to a first input; second means for varying said first astigmatic optics responsive to a second input; a patient input adjacent said patient viewing station; and, means for selectively connecting at an eye examiner station said patient input to said first input to said first variable spherical optics and to said second input to said first variable astigmatic optics.

2. The eye testing apparatus of claim 1 and including first and second view paths between said patient viewing station and said target for both eyes of said patient; second corrective optics in said view path for both eyes; said second corrective optics including second variable spherical optics to vary the spherical correction of said target along said second view path and second variable astigmatic optics to vary the astigmatic correction of said target in said second view path; third means for varying said second spherical optics connected to said second variable spherical optics and responsive to a third input; fourth means for varying said second varible astigmatic optics responsive to a fourth input connected to said second variable astigmatic optics; and wherein said means for selectively connecting said patient input further includes means for selectively connecting said patient input to said third input to said second variable spherical optics, and said fourth input to said second variable astigmatic optics.

3. The eye testing apparatus of claim 2 and wherein said first corrective optics includes first prismatic optics in at‚least one of said view paths and including fifth means for varying said prismatic optics connected to said first prismatic optics responsive to a fifth input; and wherein said means for selectively connecting said patient input includes means for selectively connecting said patient input to said fifth input to said first variable prismatic optics.

4. The eye testing apparatus of claim 2 and wherein said second corrective optics includes second prismatic optics in the other of said view paths and including sixth means for varying said prismatic optics connected to said second prismatic optics responsive to a sixth input; and wherein said means for selectively connecting said patient input includes means for selectively connecting said patient input to said sixth input to said second variable prismatic optics.

5. The eye testing apparatus of claim 1 and including first examiner input means connected to the first input to vary said first variable spherical optics and second examiner input means connected to said second input to vary said first variable astigmatic optics.

6. The eye testing apparatus of claim 1 and including an eye examiner station having a view path to said one eye of said patient and examiner eye path corrective optics in said view path between said eye examiner station and said one eye of said patient, said examiner eye path corrective optics including examiner eye path variable spherical optics corresponding to and movable with said first variable spherical optics and examiner eye path variable astigmatic optics corresponding to and movable with said first variable astigmatic optics.

7. An eye testing apparatus including in combination a patient viewing station for testing at least one eye of a patient; a target for view by said patient located along at least one view path for one eye; said target including at least one first straight line target of first preselected arbitrary angular alignment without regard to any suspected principal axis of said patient viewing station; first corrective optics in said view path between said patient viewing station and said target, said first corrective optics including first variable spherical optics to vary the spherical correction of said target and first variable astigmatic optics to vary the astigmatic correction of said target, said first variable astigmatic optics varying astigmatic lens power along first intersecting diagonals at substantially equal and opposite angles from the preselected angular alignment of said first straight line target, said first variable astigmatic optics varying said astigmatic power from positive to negative along one axis of said first intersecting diagonals and from negative to positive along the other axis of said first intersecting diagonals; first means for varying said first spherical optics responsive to a first input; second means for varying said first astigmatic optics responsive to a second input; a patient input adjacent said patient viewing station; and, means for selectively connecting at an eye examiner station, said patient input to said first input to said first variable spherical optics and to said second input to said first variable astigmatic optics.

8. The eye testing apparatus of claim 7 and including first and second view paths between said patient viewing station and said target for both eyes of said patient; second corrective optics in said other eye path between said patient viewing station and said target; said second corrective optics including second variable spherical optics to vary the spherical correction of said target along said second view path, and second variable astigmatic optics to vary the astigmatic correction of said target in said second view path, said second variable astigmatic optics for varying astigmatic lens power along a first intersecting diagonal substantially at equal and opposite angles from the preselected angular alignment of said first straight line target, said second variable astigmatic optics varying said astigmatic power from positive to negative along one axis of said first intersecting diagonal, and from negative to positive along the other axis of said first intersecting diagonal; third means for varying said second spherical optics connected to said second variable spherical optics and responsive to a third input; fourth means connected to said second variable astigmatic optics for varying said optics responsive to a fourth input; and, wherein said means for selectively connecting said patient inputs further includes means for selectively connecting said patient input to said third input to said second variable spherical optics, and said fourth input to said second variable astigmatic optics.

9. The eye testing apparatus of claim 8 and wherein said first corrective optics includes first prismatic optics in one of said view paths and including fifth means for varying said prismatic optics connected to said first prismatic optics responsive to a fifth input; and, wherein said means for selectively connecting said patient input includes means for selectively connecting said patient input to said fifth input to said first variable prismatic optics.

10. The eye testing apparatus of claim 7 and including first examiner input means connected to the first input to vary said first variable spherical optics and second examiner input means connected to said second input to vary said first variable astigmatic optics.

11. The eye testing apparatus of claim 7 and including an eye examiner station having a view path to one eye of said patient, and examiner eye path corrective optics in said view path between said examiner station and said one eye of said patient, said examiner eye path corrective optics including examiner eye path variable spherical optics corresponding to and movable with said first variable spherical optics, and examiner eye path variable astigmatic optics corresponding to and movable with said first variable astigmatic optics.

12. Eye testing apparatus including in combination a patient viewing station for testing both eyes of a patient; a target for view by said patient located along the view path to each eye of said patient; corrective optics in said view path in between said patient and said target, said corrective optics including first variable spherical optics and first variable astigmatic optics; said target projected by a projector with a first projecting lens for one eye path, and a second projecting lens for the other eye path; first means for varying the transverse position of at least one of said respective projecting lenses with respect to said eye path responsive to a first input; second means for varying said variable spherical optics responsive to a second input, and third means for varying said variable astigmatic optics responsive to a third input; a patient input adjacent said patient viewing station; an examiner's station; and, means for selectively connecting said patient input to said first input to move said projected lens and place prism in at least one of said paired eye paths responsive to said patient input, said second input to move said first variable spherical optics and said third input to move said first variable astigmatic optics, said selective connecting means located at said examiner's station.

* * * * *